United States Patent [19]
Yoon

[11] Patent Number: 5,401,247
[45] Date of Patent: Mar. 28, 1995

[54] SAFETY PENETRATING INSTRUMENT

[76] Inventor: InBae Yoon, 2101 Highland Ridge Dr., Phoenix, Md. 21131

[21] Appl. No.: 178,154

[22] Filed: Jan. 6, 1994

Related U.S. Application Data

[63] Continuation of Ser. No. 745,071, Aug. 14, 1991, abandoned, which is a continuation-in-part of Ser. No. 628,899, Dec. 18, 1990, Pat. No. 5,226,426.

[51] Int. Cl.⁶ ............................................. A61M 5/178
[52] U.S. Cl. ..................... 604/165; 604/164; 604/185; 604/274
[58] Field of Search ............... 128/753, 754, 752, 751, 128/749; 604/164, 165, 170, 158, 162, 163, 272, 274, 280, 51, 169, 117; 606/172

[56] References Cited

U.S. PATENT DOCUMENTS

| | | |
|---|---|---|
| 1,087,845 | 2/1914 | Stevens . |
| 1,147,408 | 7/1915 | Kells . |
| 1,213,001 | 1/1917 | Philips . |
| 1,248,492 | 12/1917 | Hill . |
| 1,527,291 | 2/1925 | Zorraquin . |
| 1,835,287 | 12/1931 | Donovan . |
| 2,389,355 | 11/1945 | Goland et al. . |
| 2,496,111 | 1/1950 | Turkel . |
| 2,541,542 | 2/1951 | Perez et al. . |
| 2,623,521 | 12/1952 | Shaw . |
| 2,630,803 | 3/1953 | Baran . |
| 3,540,447 | 11/1970 | Howe . |
| 3,545,443 | 12/1970 | Ansari . |
| 3,565,074 | 2/1971 | Foti . |
| 3,817,250 | 6/1974 | Weiss et al. . |
| 3,860,006 | 1/1975 | Patel . |
| 3,895,632 | 7/1975 | Plowiecki . |
| 3,993,079 | 11/1976 | de Gatztanondo . |
| 3,994,287 | 11/1976 | Turp et al. . |
| 4,013,080 | 3/1977 | Froning . |
| 4,144,884 | 3/1979 | Tersteegen et al. . |
| 4,163,446 | 8/1979 | Jamshidi . |
| 4,177,814 | 12/1979 | Knepshield et al. . |
| 4,254,762 | 3/1981 | Yoon . |
| 4,345,589 | 8/1982 | Hiltebrandt . |
| 4,379,458 | 4/1983 | Bauer et al. . |
| 4,396,021 | 8/1983 | Baumgartner . |
| 4,513,754 | 4/1985 | Lee . |
| 4,535,773 | 8/1985 | Yoon . |
| 4,601,710 | 7/1986 | Moll . |
| 4,609,370 | 9/1986 | Morrison . |
| 4,654,030 | 3/1987 | Moll et al. . |
| 4,702,261 | 10/1987 | Cornell et al. . |
| 4,733,671 | 3/1988 | Mehl . |
| 4,828,547 | 5/1989 | Sahi et al. . |
| 4,869,717 | 9/1989 | Adair . |
| 4,902,280 | 2/1990 | Lander . |
| 4,926,877 | 5/1990 | Bookwalter . |
| 4,931,042 | 6/1990 | Holmes et al. . |
| 5,030,206 | 7/1991 | Lander . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |

FOREIGN PATENT DOCUMENTS

| | | |
|---|---|---|
| 2544262 | 4/1977 | Germany . |
| 904635 | 8/1962 | United Kingdom . |
| 878265 | 11/1981 | U.S.S.R. . |
| 897224 | 1/1982 | U.S.S.R. . |

Primary Examiner—Stephen C. Pellegrino
Assistant Examiner—Guy V. Tucker

[57] ABSTRACT

A safety penetrating instrument for introducing a portal sleeve into an anatomical cavity particularly useful in least invasive surgery includes a safety probe having a distal end configuration cooperating with the sharp distal tip of a penetrating member to protect the tip in an extended position and to expose the tip in a retracted position. The configuration of the distal ends of the penetrating member and the safety probe in the retracted position form a solid, continuous surface tissue penetrating tip for the safety penetrating instrument. The safety probe and penetrating member can be removed from the portal sleeve as a unit or the safety probe can be removed while leaving the penetrating member in place for use in further procedures. The safety probe can carry interchangeable protective bodies on the distal end thereof, the bodies being made of flexible, pliable and preferably resilient materials.

8 Claims, 4 Drawing Sheets

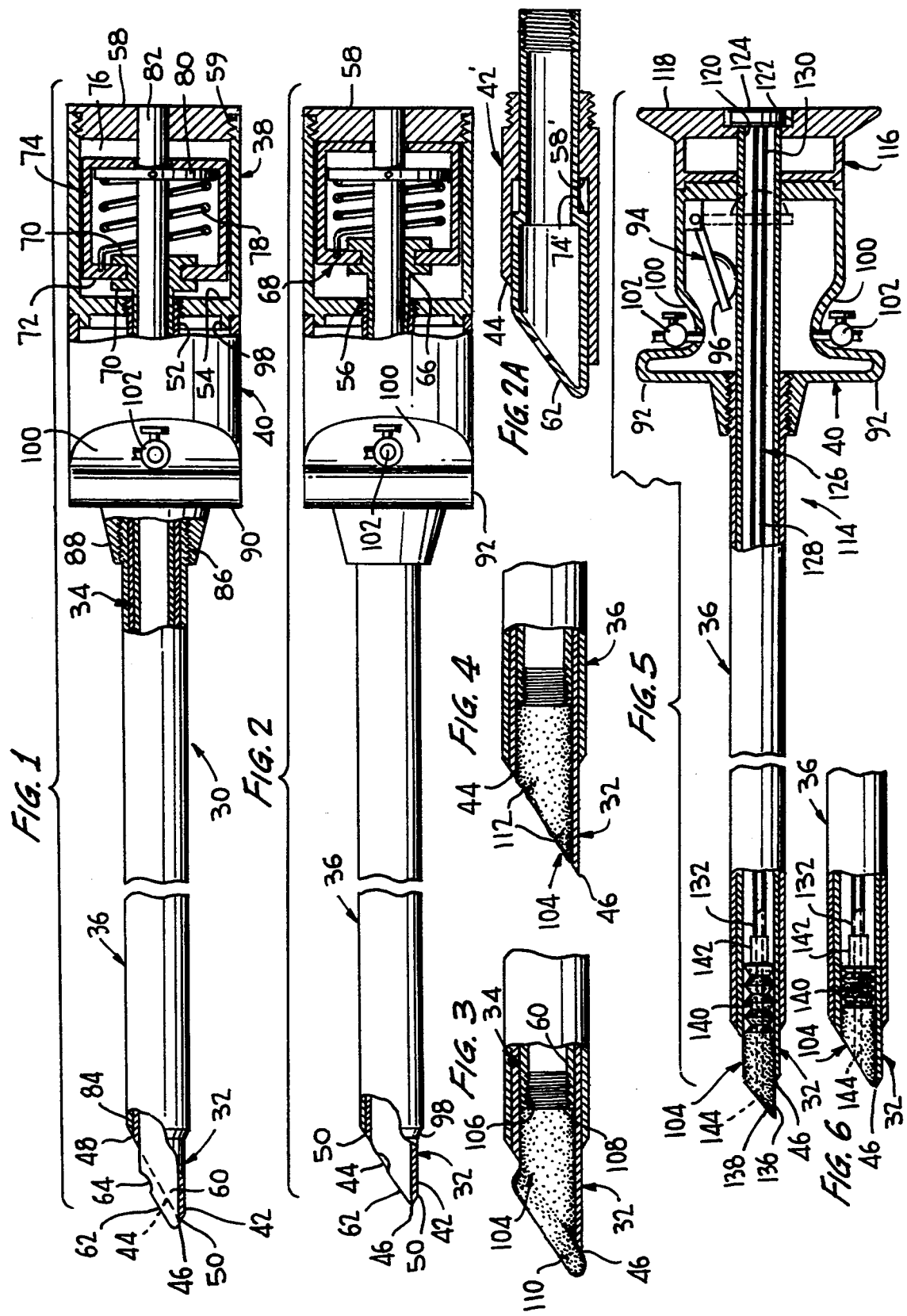

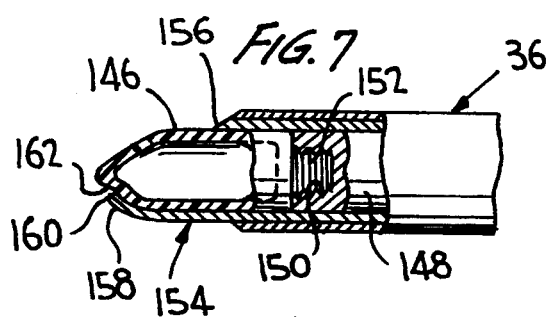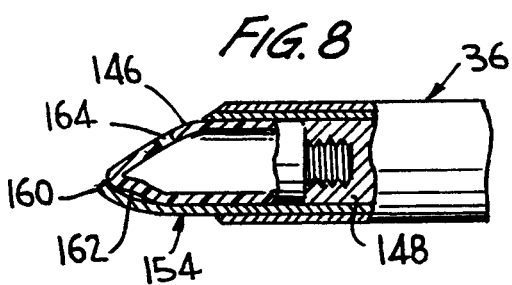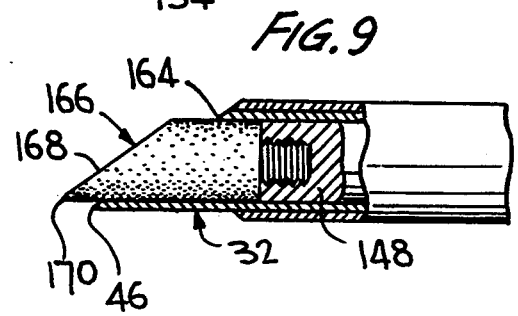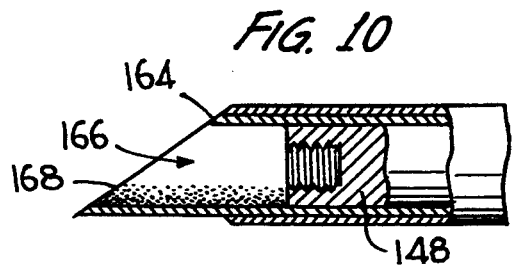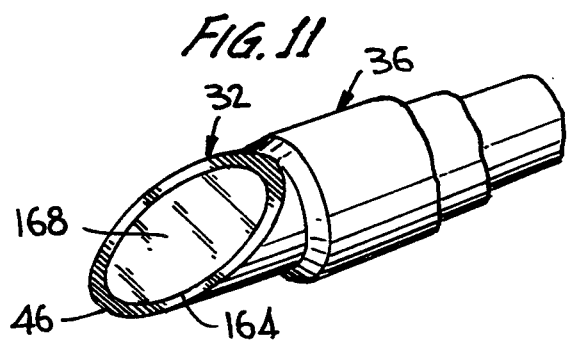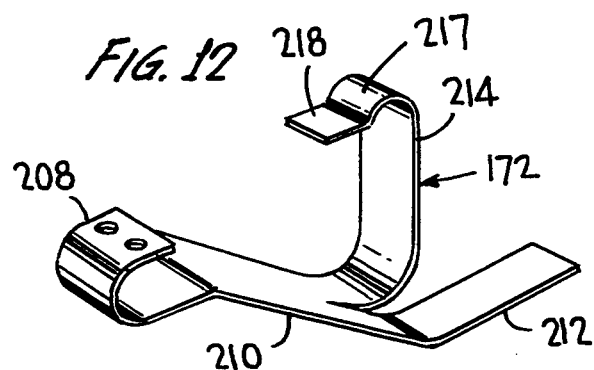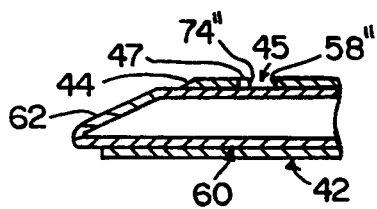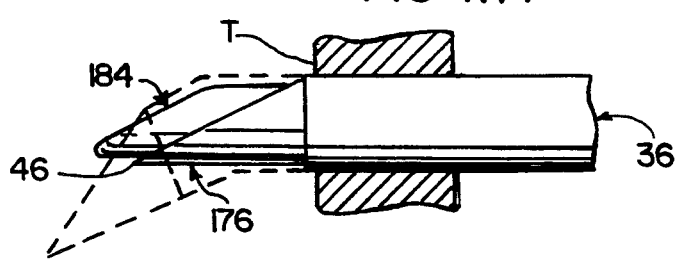

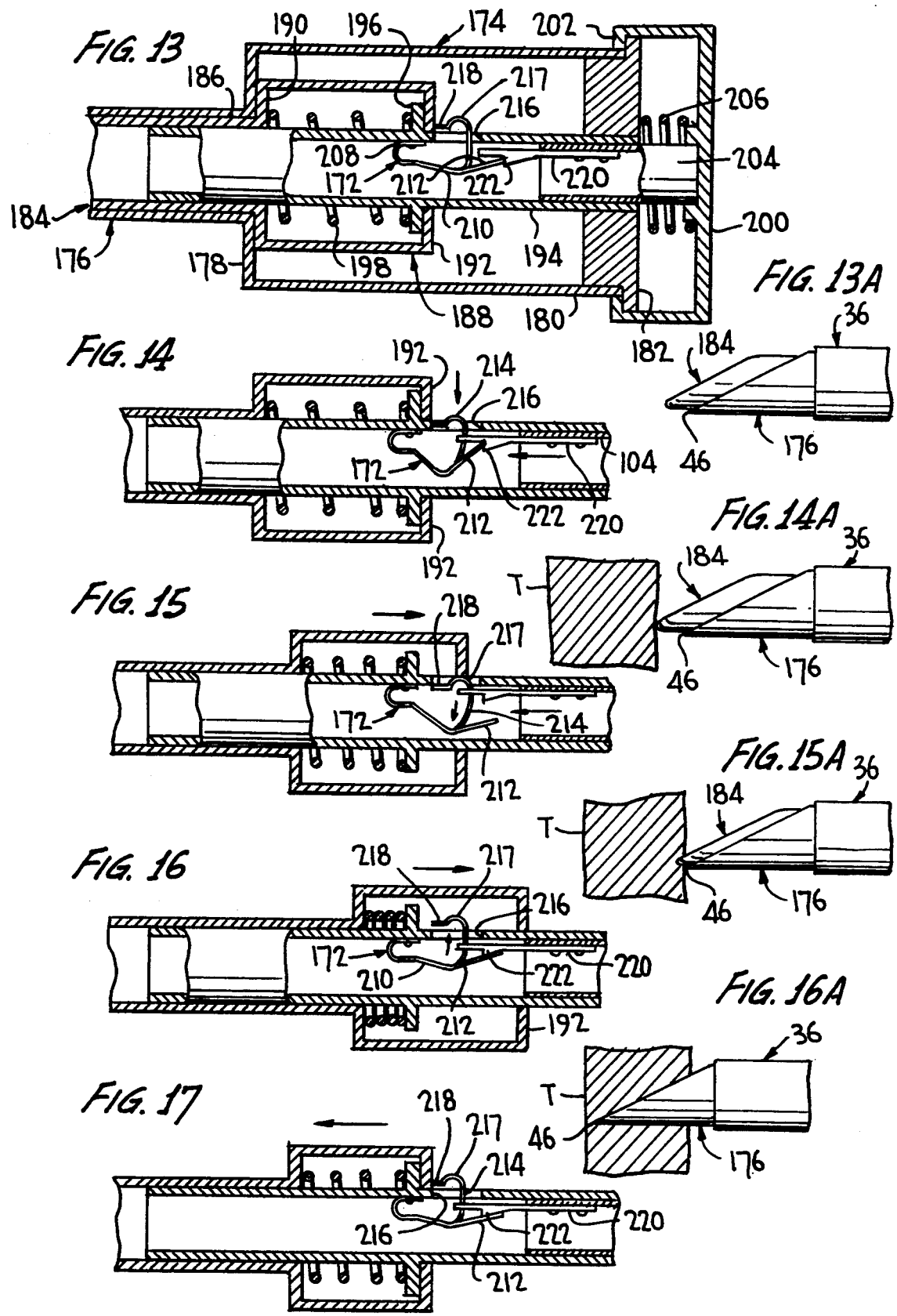

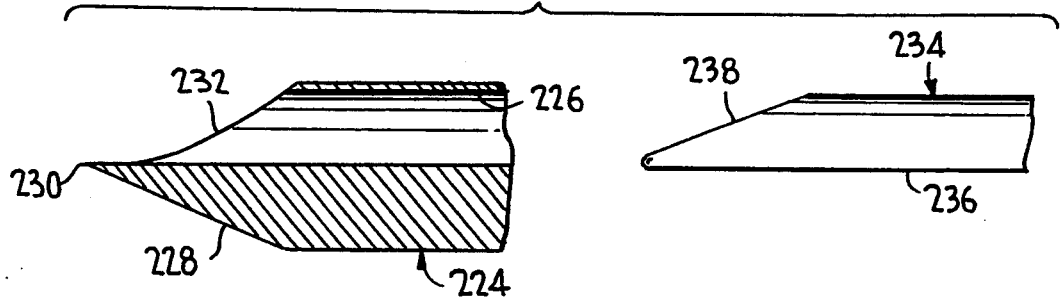
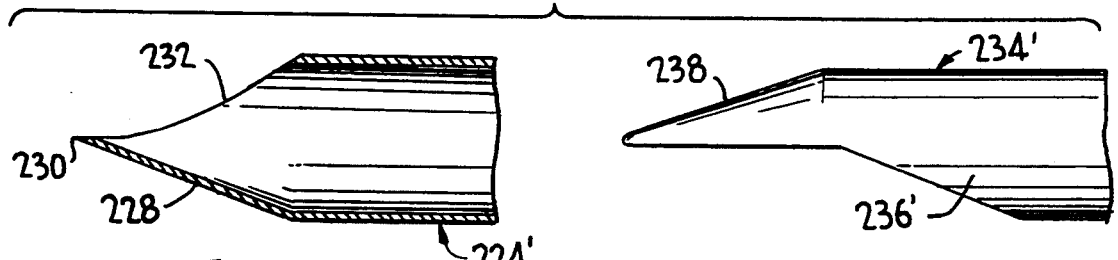
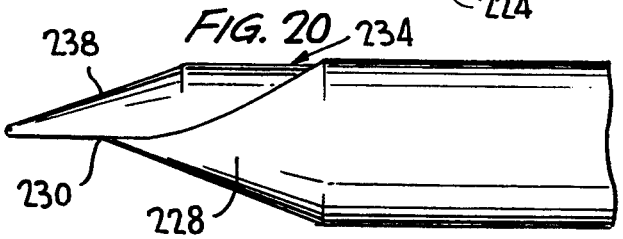
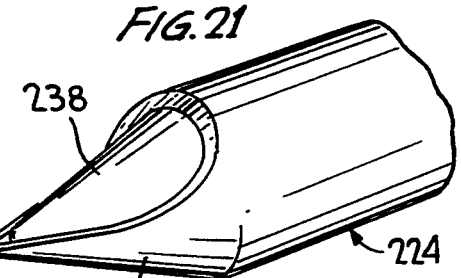
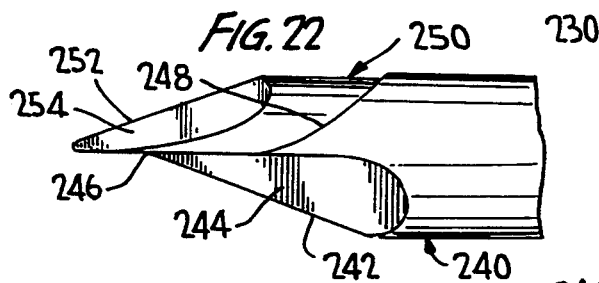
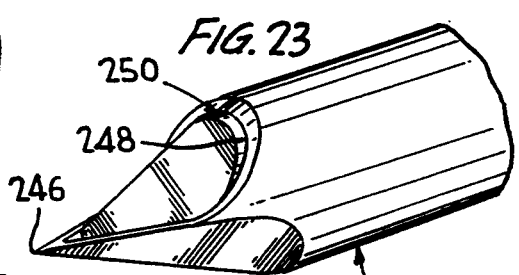
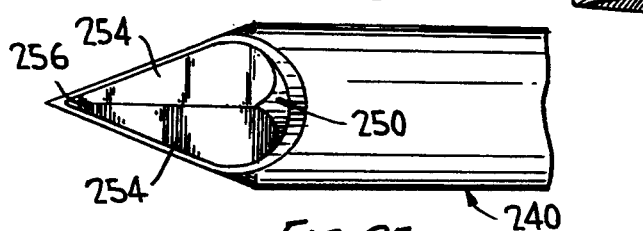
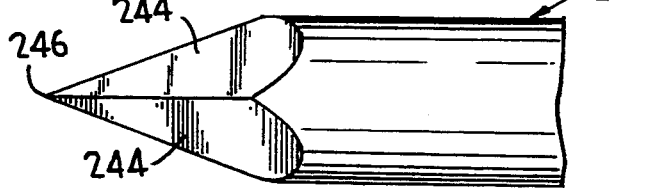

SAFETY PENETRATING INSTRUMENT

This application is a continuation of now abandoned, application Ser. No. 07/745,071, filed Aug. 14, 1991, which is a continuation-in-part of application Ser. No. 07/628,899, filed Dec. 18, 1990, now U.S. Pat. No. 5,226,426.

BACKGROUND OF THE INVENTION

1. Field of the Invention

The present invention pertains to surgical penetrating instruments and, more particularly, to safety surgical penetrating instruments having portal sleeves for establishing communication with a surgical site, elongate penetrating members with sharp tips for penetrating tissue disposed within the portal sleeves and safety probes for protecting the sharp tips of the penetrating members.

2. Discussion of the Prior Art

Surgical penetrating instruments are widely used in surgical procedures including endoscopic, or least invasive, procedures to gain access to anatomical cavities ranging in size from the abdomen to small blood vessels, such as veins and arteries, epidural, pleural and sub-arachnoid spaces, heart ventricles and spinal and synoval cavities, access being established via a portal sleeve positioned during penetration into the cavity with the safety penetrating instrument. Such surgical penetrating instruments include a penetrating member having a sharp tip or point to pierce or penetrate the tissue forming the cavity wall, and the force required to penetrate the cavity wall is dependent upon the type and thickness of the tissue of the wall. Once the wall is penetrated, it is desirable to protect the sharp tip of the penetrating member to prevent inadvertent contact with tissue in or forming the cavity, and a particular problem exists where substantial force is required to penetrate the cavity wall in that, once penetration is achieved, the lack of tissue resistance can result in the sharp tip traveling too far into the cavity and injuring adjacent tissue.

Safety penetrating instruments including a safety probe biased to extend beyond the sharp tip of a penetrating member have become widely accepted for use in penetrating anatomical cavities. For example, the Verres needle, commonly used to create a pneumoperitoneum, has a spring-loaded inner member disposed within a tubular needle. U.S. Pat. Nos. 1,527,291 to Zorraquin, No. 2,623,521 to Shaw and No. 2,630,803 to Baran are exemplary of safety penetrating instruments with a spring-loaded inner member disposed in a needle, while U.S. Pat. No. 4,254,762 to Yoon shows an endoscope spring-biased in a hollow needle. German Offenlegungsschrift 2,544,262 discloses an intrauterine catheter including a tube having a distal sharp point, a spring-biased blunt member in the tube distal end and a hose or catheter slidable over the tube. Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon, No. 4,601,710 to Moll and No. 4,654,030 to Moll et al are exemplary of such safety trocars.

While the prior art safety penetrating instruments are widely used, they suffer from many disadvantages when used in the procedures for which they are presently recommended; and, additionally, prior art safety penetrating instruments cannot be used in many procedures for which safety of penetration is highly desirable along with introduction of a portal sleeve. One of the disadvantages of prior art safety penetrating instruments is that, when the penetrating member is a tubular needle with an acutely angled distal end, the sharp tip is not well protected and is still at least partially exposed when the safety probe is in the extended position such that use in penetrating small or narrow anatomical cavities is not safe, while another disadvantage is that, when the penetrating member is solid such as a trocar, the sharp tip of the penetrating member cannot be used in further penetration of tissue after a cavity wall is initially penetrated.

SUMMARY OF THE INVENTION

Accordingly, it is a primary object of the present invention to overcome the above mentioned disadvantages of the prior art by providing a safety penetrating instrument including a portal sleeve that is useful in an expanded range of surgical procedures while increasing safety even when the penetrating member is a tubular needle.

Another object of the present invention is to limit proximal movement of a safety probe in a penetrating member to a position where a distal end surface of the safety probe is in substantial alignment with a peripheral edge of the penetrating member distal end when the safety probe is in a retracted position exposing the sharp tip of the penetrating member such that the safety probe and penetrating member distal ends present a substantially continuous surface during tissue penetration to position a portal sleeve in an anatomical cavity.

A further object of the present invention is to minimize space between distal ends of a safety probe and a hollow penetrating member, such as a tubular needle, to provide a substantially solid tissue penetrating tip for positioning a portal sleeve in an anatomical cavity.

The present invention has an additional object in the use of a flexible, pliable protective body for protecting a sharp tip of a penetrating member for positioning a portal sleeve in an anatomical cavity, the flexible, pliable material of the protective body presenting a soft surface to prevent injury to tissue contacted by the protective body. The use of a flexible, pliable material also allows the protective body to have relatively sharp edges to conform to the shape of the sharp tip of the penetrating member without causing damage to inadvertently contacted tissue.

The present invention has another object in that a protective body of a safety probe movable relative to an elongate penetrating needle within a portal sleeve is biased by means adjacent the distal end of the penetrating member toward an extended position and can move to a retracted position in response to a proximally directed force applied to the protective body from contact with tissue.

An additional object of the present invention is to form a protective body of a safety probe in a safety penetrating instrument of a resilient material such that the protective body is biased toward an extended position protruding beyond the sharp tip of a penetrating member, moves to a retracted position to expose the sharp tip in response to forces from contact with tissue during cavity penetration and returns to the extended position when the forces from tissue contact are removed due to the resilience of the material.

Yet a further object of the present invention is to permit a safety probe to be withdrawn from a tubular needle after penetration of an anatomical cavity to position a portal sleeve whereby the lumen of the needle provides a large flow path to facilitate communication with the cavity and, in particular, to facilitate aspiration of body materials, such as ovarian cysts.

An additional object of the present invention is to protect stop cocks on portal sleeve housings from inadvertent contact, bending and/or breakage during use in performing surgical procedures by positioning the stop cocks behind finger-grip flanges extending from the housing and, preferably, in recesses adjacent the finger-grip flanges.

Another object of the present invention is to control locking of a safety probe relative to a penetrating member in response to hand squeezing pressure on the hub and housing of a safety penetrating instrument.

Some of the advantages of the present invention over the prior art are that cavities of various sizes can be safely penetrated to establish a portal in communication therewith, the chance of developing a hematoma during penetration of a vein or artery is substantially reduced, second puncture endoscopic or least invasive procedures are facilitated, entry into a peritoneum is indicated by leaking fluid, safe penetration is achieved while permitting injection or evacuation of fluids, penetration into additional tissue after penetration of a cavity wall can be accomplished with a single instrument, such as into a cystic cavity or soft organ structure (e.g., ovarian cyst penetration or liver tissue biopsy), exposure of medical personnel to inadvertent contact with the sharp tip of the penetrating member is minimized, a single puncture can be used for both insufflation and forming an endoscopic portal thereby simplifying procedures such as laparoscopies, entry of the distal end of the portal sleeve into an anatomical cavity is assured prior to the safety probe returning to the extended position thereby minimizing the chances of occurrence of pro-peritoneal emphysema, and safety penetrating instruments according to the present invention can be inexpensively manufactured to permit universal use, including single patient or disposable use, in place of presently used penetrating members, such as trocars and tubular needles.

The present invention is generally characterized in a safety penetrating instrument including a penetrating member having a sharp tip, a safety probe movable relative to the penetrating member between an extended position protecting the sharp tip and a retracted position exposing the sharp tip, a hub receiving the proximal end of the penetrating member and a portal sleeve receiving the penetrating member to establish communication with an anatomical cavity upon penetration by the penetrating member. The safety probe can include a protective body made of flexible, pliable material allowing contact with the tissue within the body without injury to the tissue. Where the penetrating member is a tubular needle, the safety probe can be withdrawn from the needle after penetration into a cavity while leaving the needle in place within the portal sleeve to establish a flow path through the lumen of the needle. A positive stop can limit proximal movement of the safety probe to a position where the distal end surface of the safety probe is in substantial alignment with the distal end of a hollow penetrating member when the safety probe is in the retracted position such that the safety penetrating instrument presents a substantially continuous, solid surface during tissue penetration. Bias means can be disposed adjacent the distal end of the safety penetrating instrument and can be effected by making the protective body of a resilient material, by configuring the protective body such that a portion thereof can be compressed and expanded under its own power, and/or by contacting the protective body with a spring. A mechanism for locking movement of the safety probe relative to the penetrating member is operable by squeezing a hub receiving the safety probe and a housing receiving the portal sleeve between the fingers and palm of a surgeon's hand, and the locking mechanism can be withdrawn from the safety penetrating instrument along with the safety probe.

Other objects and advantages of the present invention will become apparent from the following description of the preferred embodiments taken in conjunction with the accompanying drawings.

BRIEF DESCRIPTION OF THE DRAWINGS

FIGS. 1 and 2 are broken side views, partly in section, of a safety penetrating instrument according to the present invention with the safety probe in the extended and retracted positions, respectively.

FIG. 2A is a broken side view of a modification of a stop mechanism for the safety penetrating instrument of the present invention.

FIG. 2B is a broken side view of a modification of a stop mechanism for the safety penetrating instrument of the present invention.

FIGS. 3 and 4 are broken side views, partly in section, of the distal end of a modification of the safety penetrating instrument of the present invention with the safety probe in the extended and retracted positions, respectively.

FIG. 5 is a broken side view, partly in section, of another modification of the safety penetrating instrument of the present invention with the hub and housing rotated 90° and the safety probe in the extended position.

FIG. 6 is a broken side view, partly in section, of the safety penetrating instrument of FIG. 5 with the safety probe in the retracted position.

FIGS. 7 and 8 are broken side views, partly in section, of the distal end of a further modification of the safety penetrating instrument of the present invention with the safety probe in the extended and retracted positions, respectively.

FIGS. 9 and 10 are broken side views, partly in section, of another modification of the safety penetrating instrument of the present invention with the safety probe in the extended and retracted positions, respectively.

FIG. 11 is a perspective view of the distal end of the safety penetrating instrument of FIG. 10.

FIG. 12 is a perspective view of a locking spring for the safety penetrating instrument of the present invention.

FIGS. 13, 14, 15, 16 and 17 are broken side views, partly in section, illustrating stages of operation of the locking mechanism of the safety penetrating instrument of the present invention.

FIGS. 13A, 14A, 15A, 16A and 17A illustrate the position of the safety probe relative to the penetrating member during tissue penetration when the locking mechanism is in the stages of operation shown in FIGS. 13, 14, 15, 16 and 17, respectively.

FIG. 18 is a broken, exploded view, partly in section, of another embodiment of a safety penetrating instrument according to the present invention.

FIG. 19 is a broken, exploded view, partly in section, of a modification of the safety penetrating instrument of FIG. 18.

FIG. 20 is a side view of the safety penetrating instruments of FIGS. 18 and 19 with the safety probe in the extended position.

FIG. 21 is a perspective view of the safety penetrating instruments of FIGS. 18 and 19 with safety probe in the retracted position.

FIG. 22 is a side view of a further modification of a safety penetrating instrument according to the present invention with the safety probe in the extended position.

FIGS. 23, 24 and 25 are perspective, top and bottom views of the safety penetrating instrument of FIG. 22 with the safety probe in the retracted position.

DESCRIPTION OF THE PREFERRED EMBODIMENTS

A safety penetrating instrument 30 according to the present invention is illustrated in FIGS. 1 and 2 and includes an elongate, hollow penetrating member in the form of a tubular needle 32, a safety probe 34 movably disposed concentrically within needle 32, an elongate, tubular portal sleeve 36 concentrically disposed around needle 32, a hub 38 mounting needle 32 and safety probe 34 and a housing 40 mounting portal sleeve 36. The hub 38 can be latched to housing 40 with the use of any suitable releasable mechanism, such as ball detents as disclosed in application Ser. No. 07/628,899, allowing the hub to be removed from the housing withdrawing the needle and safety probe from the portal sleeve. Accordingly, the safety penetrating instrument 30 may be considered to be formed of a portal unit and a penetrating unit, the portal unit including portal sleeve 36 and housing 40 and the penetrating unit including needle 32, safety probe 34 and hub 38, it being noted that the safety penetrating instrument of FIGS. 1 and 2 is preferably designed to be reusable.

Needle 32 is preferably made of a cylindrical length of stainless steel having a diameter and wall thickness dependent upon the procedure to be performed and the anatomical cavity to be penetrated. The needle has a distal end 42 terminating at a peripheral edge 44 disposed in a plane positioned at an acute angle relative to the longitudinal axis of the needle to define a sharp, tissue penetrating tip or point 46 at a leading or front edge and, proximally spaced from the leading edge, a trailing or rear edge 48. At the leading edge, the wall of the needle is ground at an angle, as shown at 50, to terminate at sharp tip 46 such that tip 46 is aligned with the inner surface of the cylindrical needle wall. Needle 32 has a proximal end 52 secured to a front wall 54 of hub 38 by any suitable means, such as threads 56 or cement.

Hub 38 is preferably made of plastic to reduce cost and has an external configuration to cooperate with housing 40 to be easily grasped with one hand for use in penetrating tissue. Hub 38 is substantially rectangular in cross-section and includes four side walls extending from front wall 54 to define a rear opening receiving a cap 58 having a configuration mating with the opening to be securely, yet releasably, mounted therein, for example by the use of threads 59.

In the embodiment of FIGS. 1 and 2, safety probe 34 is made from a cylindrical length of a rigid or flexible material, such as stainless steel or plastic dependent upon use of the safety penetrating instrument, and has a distal end 60 with a configuration to protect sharp tip 46 of needle 32 in an extended position as shown in FIG. 1. The distal end 60 has an end surface 62 with a hole 64 therein, the end surface being disposed at an acute angle to the longitudinal axis of needle 32 substantially the same as the acute angle of the needle peripheral edge 44. In this manner, the peripheral edge 44 of the distal end of needle 32 and the distal end surface 62 of safety probe 34 will be maintained in substantially parallel relation when the safety probe is in the extended position and will be positioned in substantially the same plane when the safety probe is in the retracted position as shown in FIG. 2. By grinding the distal end of the needle, the sharp tip 46 is positioned in abutment with the lateral wall of the safety probe in the extended position to be well protected and unexposed. The safety probe has a proximal end 66 disposed within hub 38 and secured to a stop member 68 movable within hub 38. The stop member can have any desired configuration to define a proximal end for abutting end cap 58 when the safety probe is in the retracted position shown in FIG. 2. As shown, the proximal end 66 of the safety probe carries spaced flanges 70 for clamping a front wall 72 of the stop member; however, the safety probe proximal end can be secured to stop member 68 in any suitable manner and can also be integrally formed with the stop member, it being of primary importance that the safety probe terminate at a proximal abutment surface providing a positive stop to limit proximal movement of the safety probe to a position where the distal end surface 62 is substantially aligned with the peripheral edge 44 of the needle to produce an essentially solid, continuous tissue penetrating tip when the safety probe is in the retracted position. The stop member, to this end, has side walls 74 extending rearwardly from front wall 72 to terminate at a rear wall 76. A helical spring 78 is mounted in compression between front wall 72 of the stop member 68 and a flange 80 secured to a tube 82 extending within safety probe 34 and having a rear end secured to end cap 58 such that the safety probe is biased distally relative to hub 38. Tube 82 provides communication entirely through the safety penetrating instrument with the penetrating and portal units assembled, and a suitable valve can be positioned at the proximal end of the safety penetrating instrument to control flow through the safety penetrating instrument.

Portal sleeve 36 is preferably made of a cylindrical length of stainless steel or other suitable, medically acceptable, plastic or metal material and can be rigid or flexible and transparent or opaque. The portal sleeve has a distal end 84 terminating at a peripheral edge disposed in substantial alignment with or forward of the trailing edge 48 of the needle such that the distal ends of the needle and the portal sleeve present a substantially smooth profile to facilitate tissue penetration and assure that the distal end of the portal sleeve is within an anatomical cavity when the safety probe returns to the extended position. The distal end 84 has a tapered, conical portion 98 disposed at the same acute angle to the longitudinal axis of needle 32 as the angle of the peripheral edge 44 of the needle such that the portal sleeve 36 smoothly follows the needle during tissue penetration. The portal sleeve 36 has a threaded proximal end 86 removably received in a threaded nipple 88 extending from a front wall 90 of housing 40. Housing 40 is preferably made of plastic and has a rectangular configuration in cross-section corresponding to the cross-sectional configuration of hub 38 with flanges 92 extending from front wall 90 to facilitate grasping with the fingers during use. A valve assembly 94, as shown in FIG. 5, is typically mounted in housing 40 to control flow through the portal sleeve once the penetrating unit is removed therefrom. The valve assembly can have any acceptable configuration and, as shown, includes a flapper valve 96 spring-biased to a closed position against an annular valve seat formed in the housing 40. Various size adapter plugs with inner sealing walls to accommodate various size instruments can be utilized to produce an effective seal for instruments varying greatly in size, for example from 2 mm to 12 mm, as disclosed in application Ser. No. 07/628,899.

In order to assemble the safety penetrating instrument 30, the penetrating unit formed by needle 32, safety probe 34 and hub 38 is combined with the portal unit by passing needle 32 through housing 40 and portal sleeve 36 moving valve member 96 away from the valve seat. With the hub 38 abutting the housing 40, a skirt 98 extending from hub front wall 54 will be disposed within the proximal end of the housing, and detents (not shown) will hold the hub in position with respect to the housing. In this position, the distal peripheral edge of the portal sleeve will be disposed substantially in alignment with or forward of the trailing edge 48 of the needle distal end to facilitate tissue penetration by the safety penetrating instrument 30.

The housing 40 has recesses 100 formed in the side walls thereof adjacent the trailing walls of flanges 92, and stop cocks 102 are positioned behind the flanges and in the recesses for controlling fluid flow through the portal sleeve since the stop cocks communicate with the housing 40 and, when the penetrating unit is withdrawn, with the portal sleeve 36. The positioning of the stop cocks behind the flanges 92 prevents inadvertent contact with and breakage of the stop cocks, and the recesses 100 increase the protection provided by the flanges and decrease protrusion of the stop cocks above the housing side walls.

The distal end of the safety penetrating instrument 30 is illustrated in FIG. 2 with the safety probe in the retracted position, and it can be seen therefrom that the end surface 62 of the distal end of the safety probe is in substantially the same plane as the peripheral edge 44 at the distal end 42 of the needle 32 with the distal end of the safety probe substantially filling the open distal end of the needle to reduce gaps between the distal ends of the needle and the safety probe and the trapping of tissue therebetween. More particularly, the safety penetrating instrument is in the state shown in FIG. 1 with the safety probe in the extended position to protect needle tip 46 prior to contact with tissue to be penetrated. When tissue contact occurs, the force on the distal end of the safety probe will overcome the force from spring 78 allowing the safety probe and stop member 68 to move proximally to the retracted position shown in FIG. 2. Proximal movement of the safety probe is limited by abutment of end wall 76 of the stop member with end cap 58 of the hub, and the space between end wall 76 and end cap 58 is the same as the space between safety probe distal end surface 62 and needle distal end peripheral edge 44 when the safety probe is in the extended position such that, the abutment of stop member 68 with end cap 58 provides a positive stop with safety probe distal end surface 62 aligned with needle distal end peripheral edge 44 and not being movable further into the needle. Accordingly, with the safety probe in the retracted position, the needle and safety probe distal ends combine to produce a solid, substantially continuous tissue penetrating tip similar to a stylet or trocar thereby preventing the trapping of tissue between the needle and the safety probe while providing the many advantages associated with the use of a cannulated penetrating member rather than a stylet or trocar including use of the needle lumen for fluid flow and irrigation/aspiration and use of the needle to penetrate additional tissue once penetration into an anatomical cavity has been achieved.

A modified stop mechanism for the safety penetrating instrument is shown in FIG. 2A wherein needle 32 has a distal end portion 42' threadedly coupled with the tubular body of the needle and carrying an internal shoulder 58' forming an abutment or stop for engaging an abutment or stop formed by external shoulder 74' on a distal end portion 60 of safety probe 34, the distal end portion being internally threaded for engagement with the body of the safety probe. The space between shoulders 58' and 74' when the safety probe is in the extended position is the same as the space between needle peripheral edge 44 and safety probe distal end surface 62 such that a positive stop is created by abutment of shoulders 58' and 74' with safety probe distal end surface 62 aligned with peripheral edge 44 when the safety probe is in the retracted position.

Another modified stop mechanism for the safety penetrating instrument is shown in FIG. 2B wherein an elongated slot 45 is formed in needle 32 at distal end 42 and a pin 47 projects radially outwardly from a distal end portion 60 of safety probe 34 to be slidably received in slot 45. Slot 45 extends longitudinally along needle 32, and a wall of needle 32 defines an abutment surface or stop 58" for engaging an abutment surface or stop 74" defined by a wall of pin 47. The space between abutment surfaces 58" and 74" when the safety probe is in the extended position is the same as the space between needle peripheral edge 44 and safety probe distal end surface 62 such that a positive stop is created by abutment of surfaces 58" and 74" with safety probe distal end surface 62 aligned with peripheral edge 44 when the safety probe is in the retracted position.

A modification of a safety probe for the safety penetrating instrument according to the present invention is shown in FIGS. 3 and 4 wherein the safety probe 34 has a protective body 104 releasably mounted on the distal end 60 thereof. The safety probe includes an elongate tubular member with a proximal end arrangement similar to that shown in FIGS. 1 and 2; however, the distal end 60 of the tubular member is open and carries internal threads 106 for receiving an externally threaded stud 108 extending from protective body 104. The protective body is made of a flexible, pliable material allowing contact with tissue within an anatomical cavity in the body without injury to the tissue even if the tissue is of a very delicate nature. The protective body can be made of various medical grade materials such as silicone rubber, latex rubber, sponge or sponge-like cellular materials or Teflon. The material is desirably compressible and expandable, soft in texture and/or resilient. The protective body 104 has a bulging or radially extending distal lip 110 such that, in the extended position shown in FIG. 3, the lip protrudes over the sharp tip 46 of the needle 32, it being noted that, contrary to the needle of FIGS. 1 and 2, the sharp tip is not ground and, thus, is aligned with the outer surface of the needle.

When the safety probe is moved to the retracted position in response to contact with tissue to be penetrated, the protective body will be moved proximally into the needle with the material compressing to allow the lip to fit in and align with the distal end of the needle as shown in FIG. 4. The material can fold or wrinkle, as shown at 112, to facilitate compression into the needle. If the material is resilient, the material itself can provide the bias for returning the safety probe to the extended position upon removal of forces from tissue contact thereby simplifying the structural arrangement at the proximal end of the safety penetrating instrument. With proper design, the amount of material compressed into the needle can act as a positive stop to prevent the distal end surface of the protective body from retracting beyond the peripheral edge of the needle distal end.

Another modification of a safety penetrating instrument 114 according to the present invention is shown in FIGS. 5 and 6 wherein needle 32, portal sleeve 36 and housing 40 are the same as shown in FIGS. 1 and 2; however, the bias spring at the proximal end of the safety penetrating instrument has been eliminated and replaced by a bias force disposed at the distal end of the safety penetrating instrument by forming protective body 104 of a resilient, flexible, pliable material and/or configuring a portion of the protective body to produce the spring or bias action. Safety penetrating instrument 114 includes a hub 116 mounted to housing 40 by detents (not shown) and having an end cap 118 with a central aperture 120 in which the proximal end of needle 32 is secured. A recess 122 surrounds aperture 120 and receives a rotating valve 124 releasably locked in the recess by any suitable mechanism, such as ball detents. A safety probe 126 is formed of an elongate tubular member 128 made of metal or plastic and having a proximal end 130 secured to valve 124 and an open distal end 132. Protective body 104 has a distal portion 136 terminating at an angled end surface 138 and a proximal portion 140 having a ribbed or accordion-like configuration terminating at a nipple 142 receiving open distal end 132 of the safety probe. A passage 144 extends through the protective body 104 such that communication is established between the distal end surface 138 of the safety probe and the proximal end of the safety penetrating instrument 114 via passage 144, elongate member 128 and valve 124 of the safety probe to provide an indication of entry into an anatomical cavity by leaking gas passing through the safety penetrating instrument. Use of the safety penetrating instrument 114 is substantially the same as discussed above with the exception that the protective body 104 is compressed upon contact with tissue during penetration to move to the retracted position shown in FIG. 6. The accordion-like proximal portion 140 folds or collapses in the retracted position; and, the accordion-like proximal portion 140 can be constructed as a positive stop such that movement of the safety probe in a proximal direction is prevented once the safety probe is in the retracted position. Once the force is removed from the protective body, the proximal portion expands to move the protective body back to the extended position protecting the sharp tip of the penetrating member.

In the modification of FIGS. 7 and 8, the protective body 146 has a bladder-like structure to be hollow, while the safety probe includes a solid, rod-like member 148 having an internally threaded distal end 150 for receiving an externally threaded stud 152 on the protective body. The protective body is made of flexible, pliable material as noted above, and a bias spring can be disposed at the proximal end of the safety probe or the material of the protective body 146 can be resilient to collapse or deflate in the retracted position. The hollow penetrating member 154 is formed by an elongate tubular needle having a distal end 156 with an open, acutely angled end defining a peripheral edge, and a portion 158 of the distal end curves toward the longitudinal axis of the needle to terminate at a sharp distal tip 160 laterally or radially displaced from the wall of the needle. The protective body 146 has a configuration to protrude over sharp tip 160 when the safety probe is in the extended position as illustrated in FIG. 7. While a smoothly curving configuration can provide protection for the sharp needle, a recess in the form of a concave portion 162 is provided in the protective body to further prevent exposure of the sharp needle tip. A hole 164 can be formed in the end surface of protective body 146 to facilitate collapse or deflation of the protective body in the retracted position and, further, for use in leaking gas from the anatomical cavity to signify penetration when the member 148 is tubular or has a passage therethrough. The safety penetrating instrument of FIGS. 7 and 8 is used in the same manner as described above; however, penetration of tissue is achieved with a scooping or rotational movement as described and shown in patent application Ser. No. 07/628,899.

The modification of FIGS. 9, 10 and 11 incorporates a rod-like safety probe member 148 with an internally threaded distal end releasably receiving a threaded stud from a protective body similar to FIGS. 7 and 8; however, the hollow penetrating member is a tubular needle with an angled peripheral edge 164 as shown in FIGS. 3 and 4. The protective body 166 is made of a soft, flexible, pliable material, such as a sponge or other sponge-like cellular material as described above; but, rather than having an end surface with rounded or curving edges, the distal end surface 168 joins the sides of the protective body at sharp edges which, due to the soft material, cannot damage tissue contacted by the protective body. Furthermore, the use of sharp edges on the protective body allows the distal end surface 168 to more completely fill the opening in the distal end of the hollow penetrating member in the retracted position as shown in FIGS. 10 and 11.

A locking mechanism for the safety penetrating instrument of the present invention includes a locking spring 172 mounted in a hub 174 as shown in FIG. 13. The hub 174 is adapted to be coupled with a housing on the proximal end of a portal sleeve as described in connection with FIG. 1, and the hub is connected with a hollow penetrating member 176 at a distal end 178 and has an open proximal end 180 releasably receiving a member 182, for example via a threaded connection (not shown). A tubular safety probe 184 is movably disposed in penetrating member 176 and has a proximal end 186 carrying a stop member 188 having a front wall 190 and a rear wall 192. A tube 194 is secured in a central aperture in member 182 and has a flange 196 disposed within stop member 188, and a helical spring 198 is mounted in compression between the stop member front wall 190 and flange 196 to bias the safety probe to the extended position relative to the penetrating member. An end cap 200 has a lip 202 extending around the periphery of member 182 such that the end cap can move longitudinally, axially relative to hub 174. A hollow stem 204 extends centrally from end cap 200 to be slidably received in tube 194, and a helical spring 206 surrounds stem 204 and is mounted in compression between end cap 200 and member 182 to bias the end cap proximally relative to the hub.

The locking spring 172 has a curved end 208 secured within tube 194 adjacent flange 196 and joined to a body 210 bifurcated to form a proximally extending deactuating arm 212 and a substantially transversely extending abutment arm 214, the abutment arm passing through an opening 216 in tube 194 and having a curved head 217 terminating at a distally extending finger 218. A deactuator or release arm 220 is mounted in stem 204 and has a protrusion 222 positioned to engage arm 212 of the locking spring.

In operation, the locking mechanism is normally in the condition shown in FIG. 13 with finger 218 disposed above tube 194 at a position to engage rear wall 192 of stop member 188 such that the safety probe 34 can not move proximally and is, therefore, locked in the extended position protecting the sharp tip 46 of the penetrating member 32 as shown in FIG. 13A.

When tissue T of an anatomical cavity wall is to be penetrated, the hub and housing are gripped in one hand with the palm of the hand engaging end cap 200; and, when the hand is squeezed, end cap 200 is moved distally along hub 174 against the bias of spring 206 causing the protrusion 222 of deactuator 220 to move arm 212 distally buckling the locking spring 172 and causing the locking arm 214 to move within the opening 216 in tube 194 and out of the path of movement of the stop member 188. Accordingly, the safety probe is now in an unlocked state and able to move proximally away from the extended position shown in FIG. 14a. When the safety penetrating instrument is forced into the tissue as shown in FIG. 15a, the safety probe will move proximally against the force of spring 198 and slide over the curved head 217 of the abutment arm of the locking spring causing the locking spring to move further into the opening of tube 194 thereby freeing arm 212 from the protrusion on deactuator 220 as shown in FIG. 15.

Once the safety probe has moved to the retracted position within the penetrating member as shown in FIG. 16a, the rear wall 192 will have passed beyond the opening 216 and out of engagement with abutment arm 114 thereby allowing the abutment arm to return to its normal position with arm 212 overlapping protrusion 222 as shown in FIG. 16.

When an anatomical cavity has been penetrated such that the force of tissue against the distal end of the safety probe is removed as shown in FIG. 17A, the safety probe will return to the extended position under the force from spring 198, camming over the curved head 117 of abutment arm 214 with the arm 214 then returning to the locking position shown in FIG. 17. At this time, the end cap 200 remains in the compressed state from gripping by the hand such that the deactuator cannot release the locking spring, and the safety probe automatically locks in the extended position. If it is desired to release the safety probe for further use of the penetrating member, the end cap must be released to return to the position illustrated in FIG. 13 whereupon squeezing the end cap again will release the safety probe for further penetration of tissue if desired.

The design of the locking mechanism allows removal of the safety probe without removing the penetrating member for purposes discussed above in that by releasing member 182 from the end of hub 174, the end cap, member 182, stop member 188 and safety probe 184 can be withdrawn from the penetrating member by moving the entire assembly proximally.

For procedures where it is desired to gain access to an area of an anatomical cavity substantially offset from the longitudinal axis of the safety penetrating instrument, the portal sleeve and the penetrating member can have a normal, non-linear configuration such that, once penetration of an anatomical cavity is completed and the safety probe is removed from the penetrating member, the portal sleeve and the penetrating member will return to the non-linear configuration. For example, the portal sleeve and penetrating member are shown in dashed lines in FIG. 17A as having a predetermined, curved configuration to which the portal sleeve and the penetrating member return when the safety probe is withdrawn.

Where the portal sleeve, the penetrating member and the safety probe are made from a flexible material, the safety penetrating instrument can be employed in flexible endoscopy wherein, for example, the safety penetrating instrument can be inserted in an operating channel of a flexible endoscope. Additionally, by forming the portal sleeve, the penetrating member and the safety probe from a flexible material, the safety penetrating instrument can be inserted through non-linear or convoluted anatomical passages.

Another embodiment of a safety penetrating instrument according to the present invention is illustrated in FIG. 18 wherein a hollow penetrating member 224 is partially solid having a passage 226 therethrough of a semi-circular configuration in cross-section. A distal end 228 of the penetrating member has a partially conical configuration terminating at a sharp tip 230 from which extends a peripheral edge 232 forming an opening in the distal end of the penetrating member. A safety probe 234 is formed of a solid elongate member 236 having a semi-circular configuration in cross-section and terminating at a distal end 236 having a partially conical configuration corresponding to the configuration of the distal end 228 of the penetrating member 224.

In the extended position, the distal end 238 of the safety probe will protrude beyond sharp tip 230 to protect the tip as shown in FIG. 20; and, during penetration of tissue, the safety probe will move to the retracted position shown in FIG. 21 such that the distal end 238 of the safety probe is positioned within the opening formed by peripheral edge 232 in substantial alignment to form, with distal end 228 of the penetrating member, a solid geometrical configuration similar to a trocar. By utilizing the positive stop mechanism illustrated in FIGS. 1 and 2 or 2A, the safety probe will be prevented from retracting further then the position corresponding with the configuration of the penetrating member such that the conical configuration of the penetrating distal end of the safety penetrating instrument is assured as shown in FIG. 21.

FIG. 19 shows a modification of the safety penetrating instrument of FIG. 18 wherein a penetrating member 224' has the same external configuration as penetrating member 184 but is tubular and the safety probe 234' has an elongate member of circular configuration in cross-section corresponding to the tubular configuration of the penetrating member. The safety penetrating instrument of FIG. 19 will assume the same configuration as the safety penetrating instrument of FIG. 18 in the extended position as shown in FIG. 20 and the retracted position as shown in FIG. 21.

A modification of the safety penetrating instrument of FIG. 18 is illustrated in FIGS. 22, 23, 24 and 25 wherein the safety probe and penetrating member cooperate to produce a solid geometric pyramid configuration. More particularly, a hollow penetrating member 240, which can be either tubular similar to the penetrating member illustrated in FIG. 19 or have a passage therethrough similar to the penetrating member illustrated in FIG. 18, has a distal end 242 having a partial geometric configuration of a pyramid with sides or facets 244 tapering to a sharp tip 246 while an opening in the distal end defined by a peripheral edge 248 terminates at sharp tip 246. A safety probe 250 has a cross-sectional configuration corresponding to that of the hollow penetrating member and has a distal end 252 formed of sides or facets 254 tapering to a narrow end 256, the configuration of the distal end 252 cooperating with the configuration of the distal end 242 of the penetrating member, when the safety probe is in the retracted position as illustrated in FIGS. 23 and 24, to produce a substantially complete geometric pyramid configuration having four sides or facets symmetrically arranged around a sharp point 246.

From the above, it will be appreciated that the safety penetrating instruments and the methods of performing procedures with the use thereof according to the present invention have many advantages in economy of construction, ease of use and expansion of medical procedures where a portal sleeve is introduced into an anatomical cavity to include a wide variety of procedures with penetration by instruments ranging in size from 2 mm to 12 mm. The design of the distal ends of the safety probe and the penetrating member to minimize the trapping of tissue therebetween is particularly advantageous for larger penetrating instruments such as those used in laparascopic procedures. In particular, by aligning the distal end surface of the safety probe with the peripheral edge of the opening in the distal end of the penetrating member when the safety probe is in the retracted position produces a continuous surface, solid distal tip for the safety penetrating instrument to facilitate use like a trocar even though a hollow penetrating member, such as a tubular needle, is used. Trocar-like use is particularly enhanced in the safety penetrating instruments of FIGS. 18-25 by the safety probe and penetrating member distal ends cooperating to form a substantially solid geometric configuration such as a cone or pyramid. Of course, any suitable solid geometric configuration for penetrating tissue can be formed including configurations with greater than four flat tapering sides or facets or with threads for gradual insertion. By causing the opening in the distal end of the penetrating member to terminate at the sharp tip, protection of the tip is assured since the safety probe distal end abuts or closely covers the sharp tip when the safety probe is in the extended position, and the use of a positive stop to limit proximal movement of the safety probes assures proper alignment of the safety probe distal end surface with the peripheral edges of the openings in the distal ends of the penetrating members. The distal end surfaces of the safety probes can protrude from the openings in the penetrating members in the retracted positions to produce desired penetrating tip configurations; however it is preferable for larger size penetrating instruments that the safety probe distal end surfaces not recede into the penetrating member openings thereby avoiding the formation of pockets in which tissue could be trapped.

The safety penetrating instruments can be constructed to be reusable or for single patient use, that is, disposable. The components can be, accordingly, made of various medical grade metals and/or plastics, and the safety probes can be tubular or solid with the penetrating members, safety probes and/or portal sleeves being rigid or flexible. The use of interchangeable protective bodies releasably or detachably secured to the safety probe permits the safety penetrating instruments to be manufactured for interchangeability in a modular fashion with particular protective bodies provided for specific procedures. Additionally, the use of interchangeable protective bodies permits the safety penetrating instruments to be partially disposable by allowing the interchangeable bodies to be discarded while the remainder of the safety instrument is suitable for reuse. By forming the protective bodies of a flexible, pliable material, such as Teflon or silicone or latex rubber, the protective bodies minimize the chance of damage to tissue inadvertently contacted and further allow the protective bodies to be configured with sharper edges to more closely conform to the distal ends of the penetrating members. Protective bodies made of soft, compressible materials, such as sponge or other sponge-like cellular materials, have the further advantages that the materials can be compressed in the penetrating members when the safety probes are in the retracted position to fill the penetrating member distal end openings and can expand when the safety probes return to the extended position such that, if desired, the protective bodies can have a shape in the extended position to protrude over or overlap the sharp tip of the penetrating member as shown in FIG. 3. When the material is resilient, the material can act as a positive stop and bias means or a spring disposed at the distal end of the safety penetrating instrument eliminating the need for the helical spring at the proximal end of the safety penetrating instrument, and the spring action can be enhanced by properly configuring the protective body, for example by using the ribbed, accordion-like shape of FIG. 5.

The various distal end configurations of the safety penetrating instruments can be used with the various proximal end configurations dependent upon procedures to be performed. For example, automatic locking may not be desirable in some situations such as where there is adhesion of organ structures, the use of a positive stop may be contraindicated where the safety probe has an additional function requiring withdrawal into the penetrating member such as for biopsy with suction and/or irrigation, and the withdrawal of the penetrating unit including the penetrating member and the safety probe may be desirable where it is desired to leave only the portal sleeve in place. Although, in most cases, the penetrating member and the safety probe are removed with the portal sleeve remaining in place, the safety probe can be withdrawn independently leaving the penetrating member in place to be used for additional procedures such as further penetration, suction and/or irrigation. When the penetrating member is left in place, the lumen of the penetrating member can be used for introduction of other surgical or diagnostic instruments to shorten operating time and the lumen can also provide a large suction passage, for example, for removal of ovarian cysts after penetration.

Having described preferred and alternative embodiments of a new and improved safety penetrating instrument, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A safety penetrating instrument comprising
an elongate, penetrating member having a proximal end and a distal end defining a sharp tip for penetrating tissue;
a safety member having a proximal end and a distal end and being movable between an extended position with said safety member distal end protruding distally of said sharp tip and a retracted position with said safety member distal end exposing said sharp tip;
hub means for receiving said proximal ends of said penetrating member and said safety member;
bias means for biasing said safety member toward said extended position and for permitting said safety member to move proximally to said retracted position in response to a proximally directed force applied to said safety member distal end, said bias means returning said safety member to said extended position when the force applied to said safety member distal end is removed;
housing means abutting said hub means;
an elongate, tubular portal sleeve surrounding said penetrating member and having a proximal end secured to said housing means and a distal end disposed adjacent said penetrating member distal end; and
locking means disposed in said hub means for controllably locking said safety member in said extended position, said locking means including an end cap movable relative to said hub means for controlling operation of said locking means in response to squeezing of said hub means and said end cap.

2. A safety penetrating instrument as recited in claim 1 wherein said locking means automatically locks said safety member in said extended position after return thereto by said bias means and said end cap is movable relative to said hub means to deactuate said locking means to allow movement of said safety member from said extended position to said retracted position.

3. A safety penetrating instrument as recited in claim 2 wherein said locking means includes a spring engaging said safety member and said end cap for locking said safety member in said extended position.

4. A safety penetrating instrument as recited in claim 3 further including a tubular member disposed in said safety member, a slot in said tubular member and a stem joined to said end cap and slidably disposed in said tubular member, and wherein said spring is disposed in said tubular member and includes a first portion projecting through said slot to engage said safety member and a second portion engaging said stem whereby movement of said end cap relative to said hub means in response to squeezing of said hub means and said end cap disengages said first portion from said safety member.

5. A safety penetrating instrument as recited in claim 1 wherein said penetrating member is hollow and said penetrating member distal end is open and wherein said safety member includes a safety probe disposed within said hollow penetrating member.

6. A method for performing a least invasive surgical procedure utilizing a safety penetrating instrument including a portal sleeve having an open distal end and an open proximal end secured to a housing, a penetrating member movably disposed in the portal sleeve and having a proximal end and a sharp tissue penetrating distal end, a safety member having a distal end and a proximal end and being movable relative to the penetrating member between an extended position protecting the sharp distal end and a retracted position exposing the sharp distal end, a hub abutting the housing and receiving the proximal ends of the penetrating member and the safety member, a locking mechanism disposed in the hub in locking engagement with the safety member preventing movement of the safety member to the retracted position and an end cap mounted for movement relative to the hub, the method comprising the steps of
contacting the wall tissue of an anatomical cavity with the safety penetrating instrument;
squeezing the hub and end cap to move the end cap relative to the hub causing the locking mechanism to be disengaged from the safety member;
forcing the safety penetrating instrument against the wall tissue while squeezing the hub and end cap causing the safety member to move to the retracted position;
introducing the safety penetrating instrument into the anatomical cavity allowing the safety member to move to the extended position and causing the locking mechanism to automatically engage the safety member; and
positioning the distal end of the portal sleeve in the anatomical cavity.

7. The method as recited in claim 6 and further comprising the step of removing the penetrating member and safety member from the safety penetrating instrument after said positioning step.

8. The method as recited in claim 6 wherein the penetrating member is hollow, the penetrating member distal end is open and the safety member is a probe movable in the penetrating member to extend through the penetrating member open distal end and further comprising the step of removing the safety probe from the safety penetrating instrument after said positioning step.

* * * * *